(12) United States Patent
Jones et al.

(10) Patent No.: US 10,342,589 B2
(45) Date of Patent: *Jul. 9, 2019

(54) PUMP

(71) Applicant: Oxford Nanopore Technologies Ltd., Oxford (GB)

(72) Inventors: Anthony Jones, Oxford (GB); Jonathan Upsdell, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/384,167

(22) Filed: Dec. 19, 2016

(65) Prior Publication Data

US 2017/0321694 A1 Nov. 9, 2017

Related U.S. Application Data

(63) Continuation of application No. 14/344,137, filed as application No. PCT/GB2012/052233 on Sep. 11, 2012, now Pat. No. 9,551,338.

(30) Foreign Application Priority Data

Sep. 15, 2011 (GB) .................................. 1116019.9
Sep. 15, 2011 (GB) .................................. 1116020.7

(51) Int. Cl.
*A61B 17/88* (2006.01)
*F04B 13/00* (2006.01)
(Continued)

(52) U.S. Cl.
CPC ..... *A61B 17/8822* (2013.01); *A61M 5/31528* (2013.01); *A61M 5/31586* (2013.01);
(Continued)

(58) Field of Classification Search
CPC ........................... F04B 13/00; A61B 17/8822; A61M 5/31586; A61M 5/31528
(Continued)

(56) References Cited

U.S. PATENT DOCUMENTS 2,461,211 A 2/1949 Guthrie
3,270,771 A 9/1966 Luke et al.
(Continued)

FOREIGN PATENT DOCUMENTS

CH 344883 2/1960
CN 101224320 7/2008
(Continued)

OTHER PUBLICATIONS

Boresi et al., Advanced mechanics of materials. 6th edition. 2003. Chapter 13. 457-501.

*Primary Examiner* — Peter J Bertheaud
(74) *Attorney, Agent, or Firm* — Wolf, Greenfield & Sacks, P.C.

(57) ABSTRACT

A pump for use in low-profile applications comprises a barrel for holding fluid; and a piston that converts a rotational driving force into a longitudinal driving motion within the barrel. The pump provides space saving advantages by reducing the need for external equipment and mechanisms around the pump for providing actuation or moving the actuating mechanism.

20 Claims, 5 Drawing Sheets

(51) Int. Cl.
*A61M 5/315* (2006.01)
*F04B 9/02* (2006.01)
*F04B 7/06* (2006.01)
*F04B 17/03* (2006.01)
*F04B 53/14* (2006.01)
*A61M 5/145* (2006.01)
*B29L 31/26* (2006.01)

(52) U.S. Cl.
CPC .................. *F04B 7/06* (2013.01); *F04B 9/02* (2013.01); *F04B 13/00* (2013.01); *F04B 17/03* (2013.01); *F04B 53/143* (2013.01); *A61M 5/145* (2013.01); *A61M 5/31513* (2013.01); *B29L 2031/26* (2013.01)

(58) Field of Classification Search
USPC ........................... 417/415; 604/211, 218, 224
See application file for complete search history.

(56) References Cited

U.S. PATENT DOCUMENTS

| | | | |
|---|---|---|---|
| 3,422,848 | A | 1/1969 | Liebman et al. |
| 3,799,411 | A | 3/1974 | Carpenter |
| 4,712,583 | A | 12/1987 | Pelmulder et al. |
| 5,496,009 | A | 3/1996 | Farrell et al. |
| 5,529,280 | A | 6/1996 | Satoh et al. |
| 5,771,935 | A | 6/1998 | Myers |
| 5,800,405 | A | 9/1998 | McPhee |
| 5,902,276 | A | 5/1999 | Namey |
| 6,004,300 | A | 12/1999 | Butcher et al. |
| 6,067,864 | A | 5/2000 | Peterson |
| 6,090,081 | A | 7/2000 | Sudo et al. |
| 6,254,057 | B1 | 7/2001 | Pubben et al. |
| 6,537,451 | B1 | 3/2003 | Hotier |
| 6,565,535 | B2 | 5/2003 | Zaias et al. |
| 7,360,556 | B2 | 4/2008 | Mijers |
| 7,537,437 | B2 | 5/2009 | Muramatsu et al. |
| 7,682,356 | B2 | 3/2010 | Alessi et al. |
| 7,766,028 | B2 | 8/2010 | Massengale et al. |
| 8,123,756 | B2 | 2/2012 | Miller et al. |
| 8,162,006 | B2 | 4/2012 | Guala |
| 8,312,805 | B1 | 11/2012 | Blume |
| 9,194,504 | B2 | 11/2015 | Cormier et al. |
| 9,551,338 | B2 * | 1/2017 | Jones ........................ F04B 9/02 |
| 9,593,370 | B2 | 3/2017 | Jones |
| 10,036,065 | B2 | 7/2018 | Jones |
| 10,054,234 | B2 | 8/2018 | Jones et al. |
| 2001/0035516 | A1 | 11/2001 | Nichols et al. |
| 2002/0007139 | A1 | 1/2002 | Zaias et al. |
| 2003/0116206 | A1 | 6/2003 | Hartshorne et al. |
| 2005/0227239 | A1 | 10/2005 | Joyce |
| 2006/0069356 | A1 | 3/2006 | Witowski |
| 2006/0105461 | A1 | 5/2006 | Tom-Moy et al. |
| 2007/0163656 | A1 | 7/2007 | Mijers |
| 2007/0202008 | A1 | 8/2007 | Schembri et al. |
| 2007/0219508 | A1 | 9/2007 | Bisegna et al. |
| 2008/0003147 | A1 | 1/2008 | Miller et al. |
| 2008/0032290 | A1 | 2/2008 | Young |
| 2009/0311117 | A1 | 12/2009 | Gustafsson |
| 2010/0062446 | A1 | 3/2010 | Hanafusa |
| 2010/0070069 | A1 | 3/2010 | Hofstadier et al. |
| 2010/0113762 | A1 | 5/2010 | Ball et al. |
| 2010/0148126 | A1 | 6/2010 | Guan et al. |
| 2011/0108147 | A1 | 5/2011 | Carmody et al. |
| 2013/0217106 | A1 | 8/2013 | Jones |
| 2014/0238497 | A1 | 8/2014 | Jones et al. |
| 2014/0314594 | A1 | 10/2014 | Jones et al. |
| 2014/0377108 | A1 | 12/2014 | Jones et al. |
| 2015/0031020 | A1 | 1/2015 | Jayasinghe et al. |
| 2019/0032798 | A1 | 1/2019 | Jones et al. |

FOREIGN PATENT DOCUMENTS

| | | |
|---|---|---|
| CN | 201152237 | 11/2008 |
| DE | 202004009831 | 8/2004 |
| DE | 102006026220 B4 | 12/2007 |
| DE | 202007012680 | 1/2008 |
| DE | 102009006203 A1 | 4/2010 |
| EP | 0086073 | 8/1983 |
| EP | 0247824 | 12/1987 |
| EP | 0925798 B1 | 6/1999 |
| EP | 0934757 | 8/1999 |
| EP | 1197693 | 4/2002 |
| EP | 1640168 | 3/2006 |
| EP | 1946793 | 7/2008 |
| EP | 2163273 B1 | 3/2010 |
| EP | 2165723 A1 | 3/2010 |
| FR | 2947873 A1 | 1/2011 |
| GB | 840499 | 7/1960 |
| GB | 896056 | 5/1962 |
| GB | 2443260 | 4/2008 |
| GB | 2447043 | 9/2008 |
| GB | 2474073 | 4/2011 |
| JP | 06-319801 | 11/1994 |
| JP | 2003-235974 | 8/2003 |
| JP | 2003-328420 | 11/2003 |
| WO | WO 1981/001445 | 5/1981 |
| WO | WO 2003/017020 | 2/2003 |
| WO | WO 2005/005829 A1 | 1/2005 |
| WO | WO 2005/017356 A1 | 2/2005 |
| WO | WO 2007/054233 | 5/2007 |
| WO | WO 2007/102836 A1 | 9/2007 |
| WO | WO 2007/141058 A1 | 12/2007 |
| WO | WO 2008/008974 | 1/2008 |
| WO | WO 2008/111863 | 9/2008 |
| WO | WO 2009/020682 A2 | 2/2009 |
| WO | WO 2009/077734 A2 | 6/2009 |
| WO | WO 2010/083147 | 7/2010 |
| WO | WO 2011/067559 | 6/2011 |
| WO | WO 2012/042226 | 4/2012 |

* cited by examiner

Fig. 3a
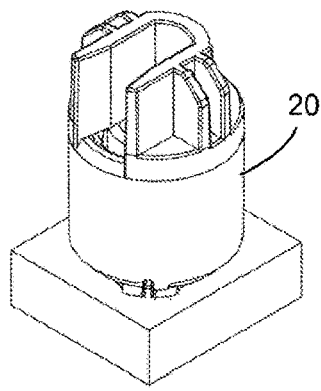
Fig. 3b
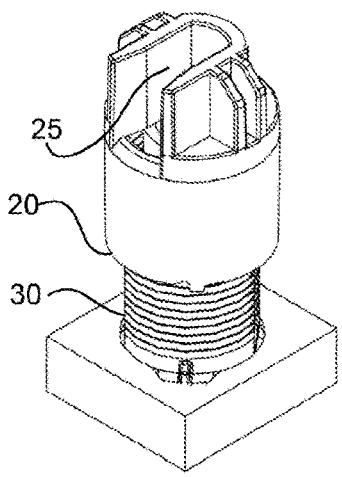
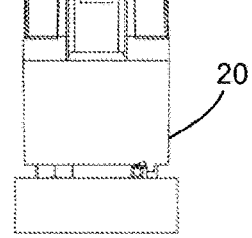
Fig. 4a
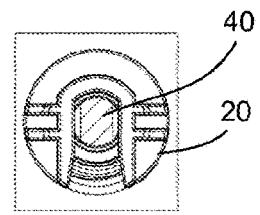
Fig. 4b
SECTION D-D

PUMP

RELATED APPLICATIONS

This Application is a continuation of U.S. application Ser. No. 14/344,137, filed on Jul. 1, 2014, which is a national stage filing under U.S.C. § 371 of PCT International Application No. PCT/GB2012/052233, which has an international filing date of Sep. 11, 2012, and claims foreign priority benefits under 35 U.S.C. § 119(a)-(d) or 35 U.S.C. § 365(b) of Great Britain Application Serial No. 1116020.7, filed on Sep. 15, 2011, and Great Britain Application Serial No. 1116019.9, filed on Sep. 15, 2011, the contents of each of which are incorporated herein by reference in their entireties.

FIELD OF INVENTION

The present invention relates to pumps and how to provide a low-profile pump for dispensing small amounts of fluid.

BACKGROUND

Syringe pumps provide a mechanism for controlling the motion of the piston within the barrel and therefore the displacement of fluid in the syringe. The syringe used by the pump may be an integral part of the pump itself, or can commonly be a disposable part that can be used and replaced, and may be a syringe that can also be used manually. A syringe pump theoretically allows for a straightforward determination of the amount of fluid pumped, based on the distance moved by the piston within the barrel.

Conventional syringes and syringe pumps operate by the motion of a plunger displacing fluid within a barrel. When the plunger is advanced from an end within the barrel, fluid in the barrel is forced out the other end. On the other hand, when the plunger is drawn out of the barrel through one end, fluid is drawn into the barrel through the other end. To allow the pumping operation to occur properly, the plunger is sealed against the barrel, so that fluid cannot pass around the plunger for example.

The syringe pump can include an actuator attached to the end of the piston plunger in order to push and/or pull the plunger in/out of the syringe barrel. In such cases, it is necessary for the actuator to move with the piston, and therefore space has to be provided for this. Further, a driving mechanism for moving the actuator needs to be provided. As a result, the syringe pump often requires much more space than the syringe which it drives. For example, the overall length/height of a syringe pump can include the length of the syringe, the length of the actuator and the length of the driving mechanism.

Other syringe pumps do not directly connect an actuator to the syringe plunger. Instead, the actuator may be driven to contact and push the end of a syringe plunger without becoming connected to the syringe. This allows for the syringe to be emptied by the pump, but not filled. In such cases, the syringes may be replaced when emptied or manually re-filled. Another problem with such pumps is that the user cannot always be certain if the pump is dispensing fluid when the actuator is displaced, because the actuator may not be in contact with the syringe plunger when the actuator is first moved.

Conventional syringe pumps also suffer from a problem related to the seal formed by the syringe plunger with the syringe barrel.

One common method of sealing the plunger against the barrel in disposable syringes is by using an elastic seal such as an O-ring. Such an O-ring is provided around the outside of the plunger, close to the end of the plunger driving fluid within the barrel. The O-ring provides a relatively deformable surface that can thus shape itself to the barrel and form a tight seal. As such, the O-ring is positioned between the plunger and the barrel and so is in contact with the fluid in the barrel.

Another method of sealing the plunger against the barrel is for the whole plunger head to be made of an elastic material, so that the plunger head deforms as a whole to produce a seal within the barrel.

In both of these cases, the fluid in the barrel is in contact with the elastic material that is being used to create the seal. This raises possible fluid contamination/interaction issues. In fluidic and microfluidic applications, and biological fluidic applications in particular, it is undesirable to introduce materials into the system which might somehow react with the fluids or leach contaminants into the process fluids and somehow affect the experiment being performed in an unexpected and/or unquantifiable manner.

Further, the use of an elastic sealing material causes a characteristic stick/slip jump when first moving the plunger. This is caused due to high static friction between the elastic sealing material and barrel, which must be overcome to start the plunger moving. The high static friction means a correspondingly large force is required to start moving the plunger, and a characteristic jerk occurs before smooth plunger motion can be observed once enough force has been applied to the plunger to overcome the static friction. Even after the static friction has been overcome, the presence of the elastic O-ring results in a relatively large amount of dynamic friction (and hence a corresponding large required driving force) that must be overcome to keep the plunger moving. This makes fine control of the syringe difficult, especially when first beginning to move the plunger.

Further, it is typical for conventional syringes and syringe pumps to somewhat rely upon deformation of the outer barrel around the piston seal (be it an O-ring or the entire piston head) to achieve a good seal. That is, the barrel will deform slightly outwards in the region of the seal to allow the piston to be moved whilst maintaining pressure on the seal.

An alternative to the elastic material approach is to make the syringe (from metal for example) so the piston is an exact fit for the barrel. However, this approach is expensive and is therefore not well suited to the mass manufacture of disposable syringes. The use of metal may also introduce fluid contamination considerations.

SUMMARY OF INVENTION

The present invention aims to provide a syringe pump that at least partly overcomes some or all of the forgoing problems.

According to an aspect of the invention, there is provided a pump comprising: a barrel for holding fluid; and a piston for drawing fluid into the barrel and driving fluid out of the barrel, wherein the piston comprises a plunger configured to move within the barrel and a sheath configured to move around an outer surface of the barrel; wherein an inner surface of the sheath and the outer surface of the barrel have complementary screw threads so that, in use, rotating the piston causes the piston to travel along the barrel. That is, rotating the piston causes the plunger and sheath to travel along the barrel.

According to this aspect, a pump having a piston that translates a rotational actuation force into a longitudinal pumping motion is provided. This avoids the need to provide any extra hardware or mechanisms to linearly actuate the pump, because the piston provides the rotational/linear movement conversion. Further, by providing a screw thread outside the pump barrel, rather than inside, the screw thread does not interfere with the operation of the pump itself. That is, the screw thread does not compromise the seal between the piston and the barrel, and it does not cause any loss of stroke-volume that might be encountered if the thread was placed on the inside of the barrel. As a result, the pump is more suitable for use in applications where space-saving is an important consideration. The pump is also suitable for applications requiring fine control of flow rates or pumped amounts. This is because the screw thread linking the barrel and the piston can be formed with whatever pitch is appropriate to the application. Changing the pitch of the screw thread changes the number of turns required to move the piston a particular longitudinal distance. Therefore, the pitch can be changed to provide very fine control, for example, by requiring many turns to move the piston a short longitudinal distance.

The pump can further comprise a piston head for forming a seal against an inner surface of the barrel, wherein the piston head is connected to the plunger of the piston so that the piston head is free to rotate with respect to the plunger or the barrel. In some situations, for example, this allows the piston head to move longitudinally within the barrel without needing to rotate with respect to the barrel. That is, the piston head can be rotationally stationary with respect to the barrel whilst rotating with respect to the piston and plunger. In general, the provision of another possible point of rotation (i.e. between the piston head and the plunger) allows for the piston head to slip against the surface of least resistance—be that the surface of the barrel or the surface of the plunger. As such, the piston head will slide against the surface of least resistance and therefore minimise the rotational frictional load, thereby reducing the driving force required to move the piston.

The pump can be configured to resist rotation of piston relative the barrel at a predetermined position. The sheath can be provided with a lug for resisting rotation of the piston relative to the barrel when the lug is brought into contact with another portion of the pump. This provides a hard stop for the piston, for example close to (or at) the point the piston head reaches the end of the barrel, without jamming the screw mechanism between the piston and the barrel. It also provides a mechanism for aligning the pump piston with respect to the barrel, which can be useful when configuring the pump for engagement with an actuating member. It also enables a known position of the piston to be determined within the plunger, if for some reason the position becomes unknown (e.g. if a position tracking system fails).

The plunger can be hollow. The piston can comprise an engagement section for engaging with a driving member and enabling the driver to turn the piston. The engagement section can comprise an opening into the hollow plunger. This allows for an actuating member, that engages with the engagement section to be received inside the hollow plunger. This in turn allows for longitudinal motion of the piston relative to the actuating member, and so avoids the need to provide any mechanism to longitudinally move the actuating member as the piston is moved. Instead, the piston can move around the actuating member itself.

The engagement section can comprise a slot for engaging a driving member by relative motion between the pump and the driving member in a direction substantially perpendicular to the direction of travel of the piston along the barrel. This allows the pump to be used in situations in which space in the longitudinal/pumping direction is limited, or for example where the driving member is fixed in position. The pump can be brought into engagement with the actuating member in a direction substantially perpendicular to the pumping direction, and no further linkage is required to connect the pump to the actuating mechanism. This avoids the need for a loading/engagement mechanism requiring longitudinal motion and therefore reduces the longitudinal space needed for engagement. This also allows for an analysis apparatus comprising a body and a cartridge attachable to the body, wherein the cartridge comprises the pump and wherein the body comprises a driving member for engaging with the pump by relative motion between the pump and the driving member in a direction substantially perpendicular to the direction of travel of the piston along the barrel.

The pump can further comprise the driving member. The driving member can have two flat and substantially parallel sides for engaging the engagement section. This allows for the engagement section to slide on and off the driving member easily, and simultaneously provides driving surfaces for transmitting the rotational actuation from actuating member to the piston.

The pump can be configured such that, in use, the driving member extends within the hollow plunger as the piston travels along the barrel. The driving member, in use, can move rotationally with respect to the barrel to drive the piston within the barrel. The pump can further comprise a worm gear arranged to rotate the driving member, the worm gear being arranged to rotate with an axis of rotation substantially perpendicular to the axis of rotation of the driving member. According to this construction, a motor for driving the piston, via the worm gear, can be arranged with its rotor having a rotational axis substantially perpendicularly to the rotational axis of the piston. Since motors are typically longer along their rotational axis than across their width, this allows a space saving pump arrangement which reduces the space needed along the rotational axis of the piston.

In an alternative arrangement, the pump can comprise a driving member that engages the outer surface of the piston. This configuration can maintain the space saving advantages whilst allowing the driving member to be thicker than the piston, because the driving member is not restricted by the need to fit within the piston.

According to another aspect, there is provided a system comprising, a casing; a pump comprising a barrel and a piston; and an actuator for moving the piston relative to the barrel; wherein the pump and actuator are provided within the casing; and wherein the system is configured to hold the actuator translationally stationary with respect to the casing whilst the piston is moved relative to the barrel.

According to another aspect, there is provided a system comprising, a pump comprising a barrel and a piston; and an actuator for moving the piston relative to the barrel; wherein the system is configured to hold the actuator translationally stationary with respect to the piston and the barrel whilst the piston is moved relative to the barrel.

According to this aspect, because it is not necessary to move the actuator in a translational sense, the height and therefore volume of the system can be reduced compared to a system that must leave space for the actuator to move within the case.

The system can be configured to hold the barrel translationally stationary with respect to the casing whilst the piston is moved relative to the barrel. In this case, the piston can move in a translational sense within the casing, during a pumping operation, whilst the other components are not moved in a translational sense. This allows the barrel to be easily connected to a fluidic system, for example, without the need to allow for motion of the barrel with respect to the fluidics. The actuator can be rotatable with respect to the casing, to allow driving of pump via a rotational mechanism. The barrel and/or the piston can comprise or consist of a plastics material. The barrel can comprise or consist of acrylonitrile butadiene styrene, polycarbonate, polytetrafluoroethylene, ultra-high-molecular-weight polyethylene, polypropylene, perfluoroalkoxy, poly(methyl methacrylate) or fluorinated ethylene propylene. The piston can comprise acetal and/or polybutylene terephthalate, and can further comprise glass fibre and/or polytetrafluoroethylene. The materials for both the barrel and the piston are preferably easily moulded, and provide good structural rigidity. The material of the barrel, which is in contact with the fluids entering and exiting the pump, preferably exhibits low binding with the fluids being processed, and low leaching of contaminants into the fluids. This is particularly important in biological applications, such as biological nanopore applications, in which contaminants could block pores or otherwise interact with and/or deactivate biological molecules in unexpected and undesirable ways.

According to another aspect, the invention provides a method of pumping fluid, the method comprising: providing a barrel for holding fluid; providing a piston for drawing fluid into the barrel and driving fluid out of the barrel, wherein the piston comprises a plunger configured to move within the barrel and a sheath configured to move around an outer surface of the barrel; and rotating the piston relative the barrel, along complementary screw threads provided on an inner surface of the sheath and the outer surface of the barrel, so that the piston travels along the barrel.

The method can further comprise providing the driving force for rotating the piston via a motor, wherein an output shaft of the motor has a rotational axis substantially perpendicular to the rotational axis of the piston.

BRIEF DESCRIPTION OF THE FIGURES

The present invention will be described with reference to exemplary embodiments and the accompanying Figures in which:

FIG. 3a and FIG. 3b are perspective views of the syringe pump of FIGS. 1a and 1b, with the syringe pump advanced and withdrawn respectively;

FIG. 4a is a side elevation view of the syringe pump system as show in FIG. 1a, and FIG. 4b is plan view of the system of FIG. 4a through the plane D-D;

DETAILED DESCRIPTION OF THE INVENTION

The present invention has identified that conventional syringe pumps are unsuitable for many fluidic and microfluidic applications. For example, WO 2009/077734 hereby incorporated by reference, relates to the formation of layers of amphiphilic molecules, in which nanopores can be deployed to provide an environment which can be useful, for example, for sequencing polynucleotides. This is an example of a 'nanopore application', referred to below. The formation of the bi-layer, the provision of the nanopores, and the subsequent provision of test fluids require careful control of the fluidic environment, both in mechanical and chemical terms. In the case of pumping lipid to form bi-layers, an extremely slow pumping speed is required. An example range is between 1 µl/s to 0.1 µl/s. The stick/slip issues with conventional elastic-sealing syringe pumps makes control of such flow rates extremely problematic, and can make repeatability of experiments very difficult. This is particularly relevant when considering the small volumes of liquids being displaced and the need to ensure that accurate amounts of a required fluid are provided at the correct time.

Another consideration for nanopore applications is that the presence of contaminants in the system poses a risk of blocking of the nanopores and/or interacting with biological molecules (including the biological nanopores) in an undesirable way. As such, it is desirable to minimise the number of materials in contact with the process fluids and, for those materials that will contact the process fluids, use materials that will have the minimum interaction with the fluids (e.g. exhibiting low binding with the fluids, low leaching of contaminants into the fluids). Contamination is a particular problem with biological nanopores as the pore may be temporarily or permanently deactivated. Also, other proteins in the system may be deactivated or denatured.

In addition to these considerations, the invention identifies a need to provide a pump that makes the best use of the available space. For example, WO 2011067559, hereby incorporated by reference, discloses a biochemical analysis instrument that utilises nanopores deployed in a lipid bi-layer to, for example, sequence polynucleotides. As mentioned above, the formation of the bi-layer and the provision of the nanopores require careful control of the microfluidic environment but at the same time the space available for the fluidics is limited.

Of course, many of the above considerations are not limited to nanopore applications, and are generally applicable to other fluidic and microfluidic environments.

Figure 1A:
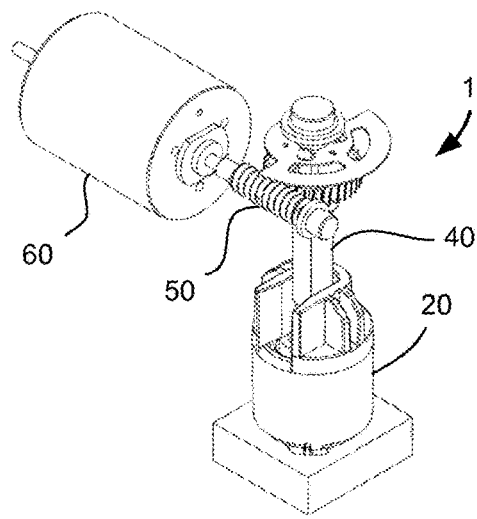
FIG. 1a and FIG. 1b are perspective views of a syringe pump system, with the syringe pump advanced and withdrawn respectively.
Figure 1B:
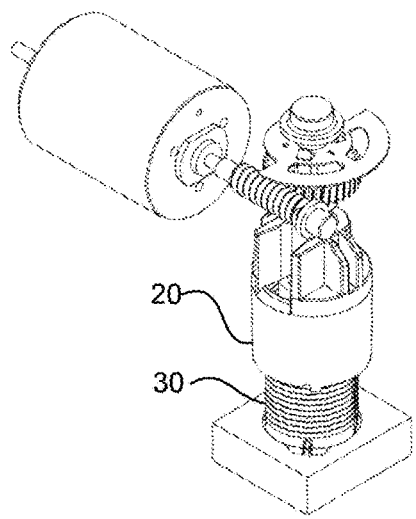

FIG. 1 shows a syringe pump system 1, which incorporates a syringe pump that comprises a piston 20 and a barrel 30, an actuation system 40, a motor 60 and a worm gear 50. The motor 60 drives the worm gear 50, which in turn drives the actuation system, which in turn drives the syringe pump. As the syringe pump is driven, the piston 20 moves with respect to the barrel 30. FIG. 1a shows the piston 20 advanced within the barrel 30, whilst FIG. 1b shows the piston 20 relatively withdrawn within the barrel 30.

Figure 2A:
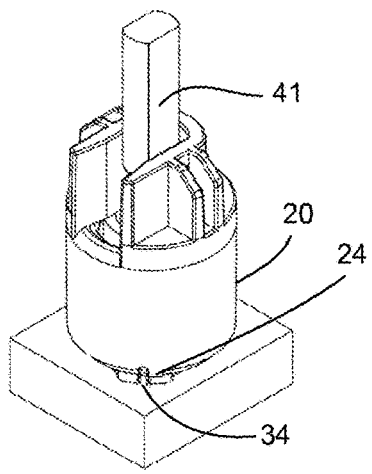
FIG. 2a and FIG. 2b are perspective views of the syringe pump and actuator of FIGS. 1a and 1b, with the syringe pump advanced and withdrawn respectively.
Figure 2B:
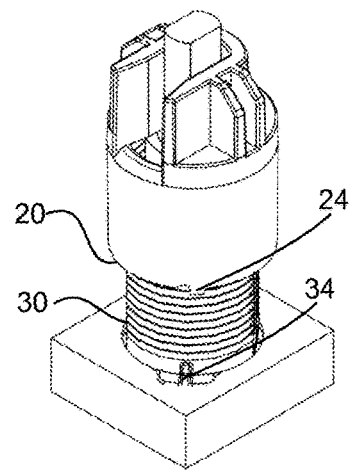
Figure 5A:
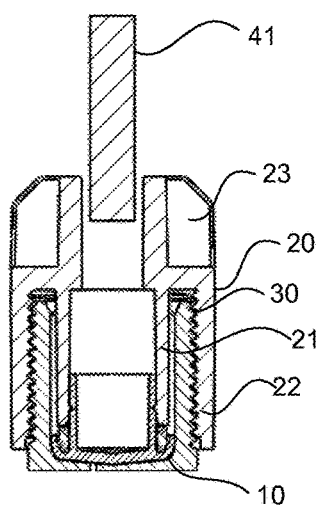
FIG. 5a and FIG. 5b are sectional views of the syringe pump of FIGS. 3a and 3b, with the syringe pump advanced and withdrawn respectively.
Figure 5B:
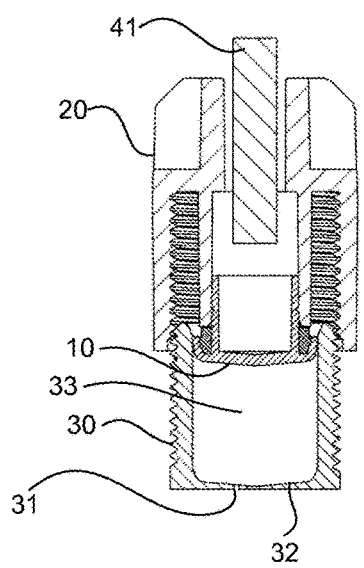

FIGS. 2a and 2b correspond to the configurations of FIGS. 1a and 1b respectively, omitting the motor 60 and worm gear 50 and only showing the driving member 41 of the actuation system 40. Similarly, FIGS. 3a and 3b correspond to the configurations of FIGS. 2a and 2b but omit the driving member 41. FIGS. 5a and 5b show cross-section views through the pump and driving member 41 as pictured in FIGS. 2a and 2b respectively.

FIG. 4a shows a side view of the pump system 1 of FIG. 1. FIG. 4b shows a cross-section view through the plane D-D as indicated in FIG. 4a.

Pumping operation of the pump assembly 1 is achieved by the motion of piston 20 driving a barrier surface/piston head 10 (discussed below) and displacing fluid within the barrel 30 in the manner of a syringe. The piston head 10 is circular in cross-section and fits snugly within the cylindrical barrel 30 so that, when the plunger 21 is advanced within the barrel 30 (i.e. moved downwards in the geometry of FIGS. 1-3) fluid in the barrel 30 is forced through an opening 31 in the barrel 30. On the other hand, when the plunger 21 is drawn out of the barrel 30, fluid is drawn in to the barrel 30 through the opening 31. In FIG. 5 the opening 31 in the barrel is shown as an orifice in the end of the barrel 30, but in alternative constructions it can be a different shape or size.

As can be seen from FIGS. 1-4, the pump consists of a barrel section 30 for holding fluid and a piston section 20 for drawing fluid into the barrel 30 and driving fluid out of the barrel 30. For fluidics or nanopore applications, the pump may be operable to produce a variety of flow rates. For example, in nanopore applications, it may be desirable for a pump to produce flow rates of from 50 to 100 μl/s for cleaning; for initially priming the fluid lines with the working fluid it may be desirable for a pump to produce flow rates of from 20 to 50 μl/s; for providing lipid for bi-layer formation it may be desirable for a pump to produce flow rates of from 0.1 to 0.5 μl/s; and for providing pores or buffer it may be desirable for a pump to produce flow rates of 1 to 3 μl/s. A single pump may be capable of producing the flow rates for each of these requirements, but individual pumps for each requirement may also be used. In general, it is desirable for the pump to produce flow rates of 0.01 μl/s or more, optionally 0.05 μl/s or more, further optionally 0.1 μl/s or more, still further optionally 20 μl/s or more and still further optionally 50 μl/s or more. Further it may be desirable for the pump to be operable to produce flow rates of 500 μl/s or less, optionally 200 μl/s or less, further optionally 100 μl/s or less, still further optionally 50 μl/s/ and still further optionally 20 μl/s or less.

The piston 20 comprises a plunger section 21 and a sheath section 22. The plunger 21 is configured to move within the barrel 30 and displace the piston head 10, whilst the sheath is configured to move around the outer surface of the barrel 30. That is, the barrel 30 fits between the plunger 21 and the sheath 22. The plunger 21 and the sheath 22 are connected to each other and are preferably formed together, for example via moulding.

This piston section 20 does not come into contact with the fluid in the barrel 30. This is because the piston head 10 is provided at the end of plunger 21. As discussed in more detail below, with reference to FIGS. 6-8, the piston head 10 provides a barrier surface which seals across the barrel 30, and so the piston 20 is isolated from the fluid.

The barrel 30 and the sheath 22 are constructed to screw together. As such, the inner surface of the sheath 22 and the outer surface of the barrel have complementary screw threads so that the piston 20 will travel along the barrel 30 as the piston 20 is rotated. Further, the screw thread prevents the piston 20 being moved with respect to the barrel 30 by a force applied in the direction of piston travel in the barrel 30.

That is, a rotational driving motion is needed to produce a linear motion of the piston 20 with respect to the barrel 30. This rotational actuation, converting the rotational movement to a linear movement via the thread, allows fine control of the movement of the piston 20, by suitable selection of the thread pitch. That is, because a 360° rotational movement is required to move the piston 20 longitudinally by one thread pitch, the thread pitch can be selected as required to give the desired level of control over the piston 20 displacement. In preferred embodiments, the thread can be pitched to provide 10 mm or less of longitudinal motion per revolution of the piston, optionally 5 mm or less per revolution, further optionally 2 mm or less per revolution and still further optionally 1 mm or less per revolution. In addition, the selection of barrel volume and gearing ratios in the actuation system further contribute to controlling the flow rates produced by the pump. The provision of the screw thread on the external surface of the barrel 30 is also advantageous. If the screw thread were provided on the inner surface of the barrel 30, it could potentially interfere with the sealing of the piston head 10 against the barrel 30. Alternatively, to avoid such interference, the length of the barrel would need to be extended to allow for the provision of a screw-section that does not overlap with stroked-volume of the barrel 30. However, this would result in a larger and more unwieldy pump, and would not be suitable for use in applications with limited space.

Preferably, the screw connection, between the barrel 30 and the piston 20, also keeps the piston 20 held rigidly in position with respect to the barrel via the thread. This is advantageous because it helps avoid variation in forces acting between the barrel 30 and the piston 20 that could be introduced if the angle of the piston 20 within the barrel 30 was able to vary, which in turn could cause unwanted forces acting on the pump and/or lead to uncertainty in the position of the piston 20 within the barrel 30. That is, flexibility in the angle of the piston 20 within the barrel 30 would mean that force could be applied into the barrel wall through the piston head and/or, for a given movement of the driving rod 41, the position of the piston 30 would not be accurately known.

The rigidity of the piston 20 with respect to its position in the barrel 30 can also be assisted by suitable material selection for the piston. This can also assist in ensuring the piston head 10 is held firmly in position. In addition, because having a thread interface introduces an efficiency loss into the pump driving system (because of the additional friction between the piston 20 and the barrel 30, compared with a conventional sliding syringe pump), material selection can help provide lubrication. Because (as mentioned above) neither the piston plunger 21 nor the piston sheath 22 comes into direct contact with the fluid being pumped, there is a low risk of the piston material causing any contamination of the fluid being pumped. Therefore, materials for the piston can be selected primarily based upon their mechanical properties. Preferably materials that could be used for the piston are acetal (i.e. polyoxymethylene or POM), or polybutylene terephthalate (PBT) with added glass fibre and/or added lubricants such as PTFE. Examples of such materials are HOSTAFORM® C9021 GV1/20 XGM and LUBRI-ONE® PS-30GF/15T/02S.

Since the barrel 30 comes into contact with the fluid being pumped, it is preferable to make the barrel material selection based upon the desire to avoid introducing contaminants. For example, in nanopore applications the presence of contaminants in the system poses a risk of blocking of the nanopores or possibly inactivating biological nanopores or other biological molecules present in the fluids being processed. As such, it is desirable to minimise the number of materials in contact with the process fluids and, for those materials that will contact the process fluids, use materials that will have the minimum interaction with the fluids (e.g. exhibiting low binding with the fluids, and low leaching of contaminants into the fluids). As a result, the plunger barrel 30 is preferably made of a plastics material for ease of manufacture and cost effectiveness, and is more preferably an easily mouldable plastics material such as acrylonitrile butadiene styrene (ABS) polycarbonate (PC) or poly(methyl methacrylate) (PMMA). Other possible materials include polytetrafluoroethylene, ultra-high-molecular-weight polyethylene, polypropylene, perfluoroalkoxy or fluorinated ethylene propylene.

For a fluidics or nanopore application, the barrel can have a volume of 10 ml or less, optionally 5 ml or less, further optionally 2 ml or less, and still further optionally 1 ml or less.

A preferable method of manufacturing the pump piston 20 and barrel 30 is by moulding, as this allows large scale manufacture with good mechanical precision at relatively low cost. To assist with moulding the threaded barrel, the thread can have two flat surfaces removed, from two opposite sides of the thread. Then, when the component is moulded, the thread can be formed via two tool halves rather than a single tool thread that needs to be unwound from the moulded product.

The piston 20 is provided with a lug 24. As can be seen in FIG. 2, the lug 24 is provided at the bottom of the piston 20, on the sheath 22, and a further lug 34 is provided in connection with the barrel 30. Movement of the piston 20 is limited by the lugs 24, 34 because lug 24 projects lower than the base of the piston 20. Therefore, the lug 24 comes into contact with the lug 34 when the piston 20 has been advanced into the barrel 30 and the piston head 10 is close to, or at, the end of the barrel 30. The point at which the lugs 24, 34 contact each other defines the limit that the piston 20 can be screwed onto the barrel 30, and so the furthest point to which the piston 20 can be advanced. That is, the lugs 24, 34 prevent the piston 20 being advanced any further, and therefore avoid over-tightening or jamming of the screw mechanism. This also allows easy initial manual positioning of the piston 20 (e.g. before engaging the pump barrel/piston assembly with the actuating assembly 40) and, when the assembly 1 is actuated, gives a hard stop on the angular position that actuation motor 60 can drive to.

As previously discussed, conventional syringe pumps commonly seal the plunger against the barrel with an elastomeric seal such as an O-ring. Such an O-ring is provided around the outside of plunger, and is conventionally in contact with the fluid in the barrel. When emptying the pump, the seal helps prevent fluid from flowing around the plunger rather than through the orifice in the barrel. When filling the pump by drawing fluid through the orifice, the seal helps reduce air from the pump surroundings being drawn into the barrel around the plunger and so ensures that fluid is drawn in through the orifice. The seal is conventionally at least partly maintained by the syringe barrel flexing around the plunger and thus pushing inwardly onto the plunger as the plunger is moved through the barrel. However, the flexibility of the barrel introduces an inherent lack of accuracy in the syringe design, because the volume of the barrel changes as the plunger is moved, and therefore the volume of fluid expelled from (or drawn into) the barrel is not known accurately. Preferably the barrel is substantially rigid.

Figure 6:
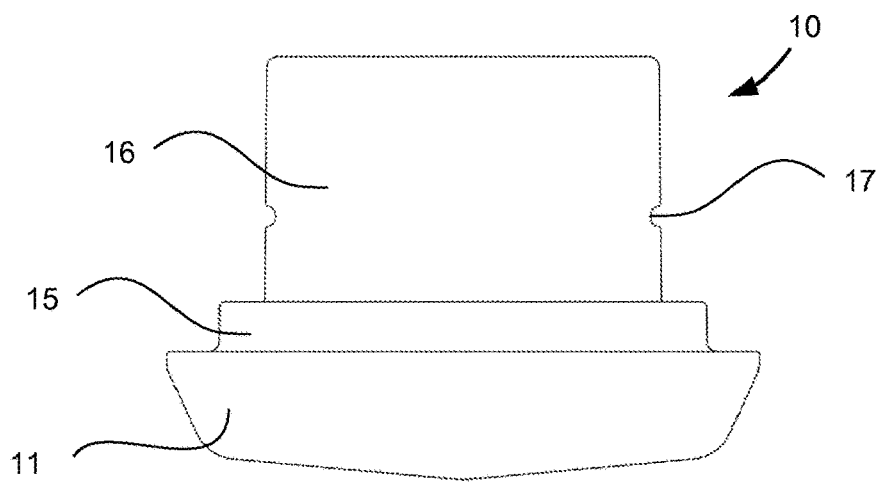
FIG. 6 is schematic diagram of the plunger head of the syringe pump of FIG. 5.
Figure 7:
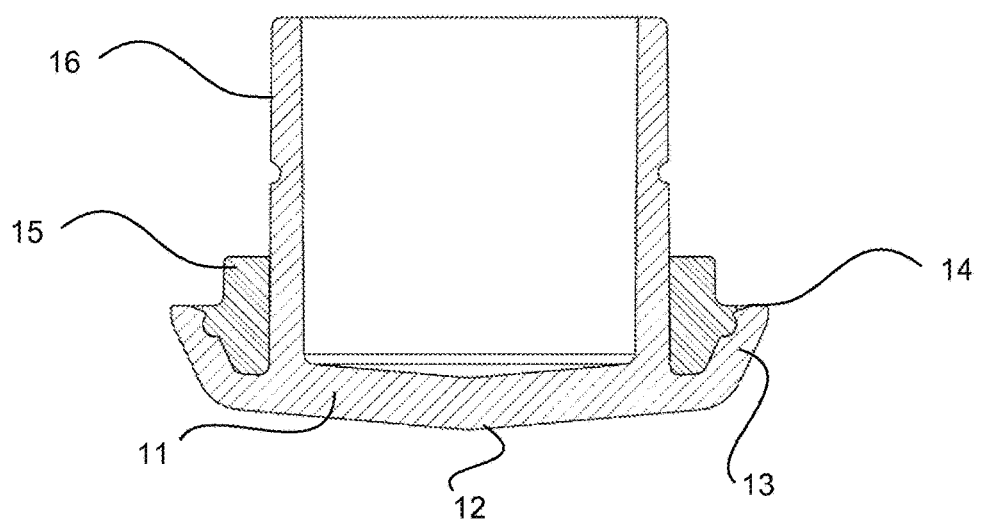
FIG. 7 is a cross-sectional view of the plunger head of FIG. 6.
Figure 8:
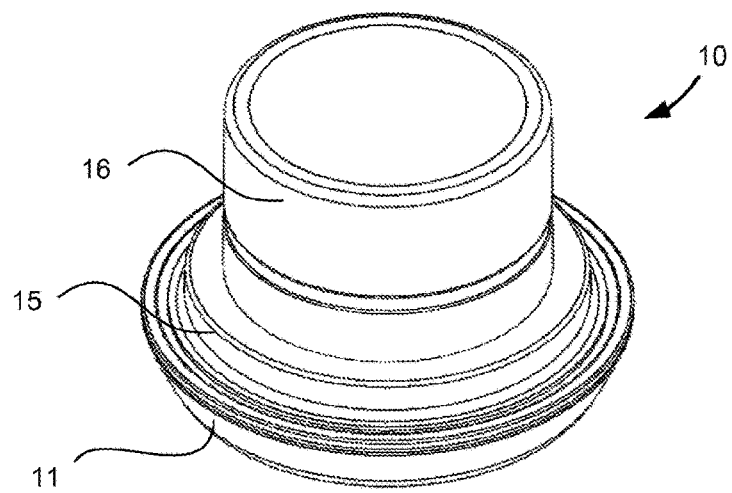
FIG. 8 is a perspective view of the plunger head of FIG. 6.

The piston head 10 is shown in detail in FIGS. 6 to 8. In contrast to conventional pistons, the piston head 10 has a piston seal that seals against the barrel 30 differently.

In the Figures, the piston head 10 fits to the end of the plunger 21, a ridge on an inner surface of the plunger clipping over the depression 17 formed in the piston head. This construction is preferable, because the piston head 10 can remain free to rotate with respect to the plunger 21 and/or the barrel 30. This reduces friction within the pump as it is actuated, because piston head 10 only needs to rotate with respect to the surface presenting the least resistance. That is, the piston head 10 is free to rotate with respect to whichever of the plunger and the barrel presents the least frictional resistance to rotation, and is not forced to rotate with respect to the higher friction element (whichever it is). Of course, the skilled person will appreciated that the same advantage can be achieved by providing a depression on the inner surface of the hollow plunger 21 and a corresponding ridge on the body of the piston head 10.

However, any suitable method of attaching the piston head 10 to a plunger 21 may be used. In some constructions, especially if friction is not a particular concern, the piston head 10 might not be separate to the plunger 21; that is, the piston head 10 can be formed integrally with the body of the plunger 21 itself.

The piston head 10 has piston seal comprising a barrier portion 11 that forms a barrier across the barrel 30. The barrier portion 11 has a barrier surface 12 that faces the fluid being displaced within the barrel (whether that fluid is being driven out of the barrel 30 or drawn into the barrel 30).

The peripheral portion of the barrier portion 11 (that is, the radially outermost portion) is formed into a lip 13, which projects from the opposite side of the barrier portion 11 to the barrier surface 12. In the figures, the lip 13 stands proud from the upper surface of the barrier portion 11, projecting upwards whilst the barrier surface (which contacts the liquid in the syringe barrel) faces downwards. That is, the lip 13 is formed by the edge of the barrier portion 11 retreating back in the direction of the plunger 21 and away from the base 32 of the barrel 30. As such, the lip 13 extends and projects at least partially around resilient member 15 (discussed in more detail below). However, the lip 13 still at least partially extends outwards in a radial direction from the centre of the pump head 10. As such, the barrier surface 12 has a slightly convex shape with respect to the barrel chamber 33 (i.e. a convex shape when the barrier surface 12 is viewed directly), especially in the vicinity of the inner surface 34 of the barrel 30 and the point at which the lip 13 merges into the bulk of the barrier portion 11.

The widest diameter of the piston seal occurs on the outer surface of the lip 13 (i.e. the continuation of the barrier surface 12). For fluidics or nanopore applications, the widest outer diameter of the piston seal may be 50 mm or less, optionally 25 mm or less, and still further optionally 15 mm or less. In a preferred embodiment, the outer diameter is 11.6 mm. Further, the outer diameter may be 1 mm or more, optionally 3 mm or more, further optionally 5 mm or more and still further optionally 10 mm or more. At rest, when the piston head 10 is not assembled into a corresponding barrel 30, this widest diameter of the pump seal is wider than the inner diameter of the barrel 30. As such, when the pump head 10 is inserted into the barrel 30, the lip 13 is deflected inwardly (i.e. towards the centre of the pump head). That is, the pump head 10 deforms to allow insertion into the barrel 30.

The barrier portion 11 of the pump head 10 is preferably sufficiently rigid, such that it will resist the deflection of the lip 13 and hence force the lip 13 against the barrel 30 and form a seal around the piston head 10. The barrier portion may be made of plastic or a material other than plastic, such as a metal. However metals are generally too inflexible to be suitable and are generally not preferred, unless provided for example as a thin layer or coating on the resilient member. Another reason plastics are preferred is because they are typically cheaper than metals.

Another reason plastics might be preferred over metals would be if there are concerns regarding metals reacting with or contaminating the fluid being pumped. For example, in lab-on-a-chip applications, such as nanopore applications, it is desirable to minimise fluid contamination and so plastics materials are often more suitable for constructing fluidic and microfluidic circuits than metals. Similarly, to avoid contamination when using plastics for the piston head 10 it is preferable to use plastics which exhibit low chemical/plasticiser leaching. Preferable plastics include polytetrafluoroethylene (PTFE), ultra-high-molecular-weight polyethylene (UHMWPE), polypropylene (PP), high density polyethylene (HDPE), perfluoroalkoxy (PFA) or fluorinated ethylene propylene (FEP).

The use of substantially rigid material for the barrier portion 11 circumvents the need for flexible barrel to help form the seal. Instead, the seal can be formed by the deflection of the barrier portion 11 against the barrel 30. However, the use of rigid materials such as plastics for the barrier portion 11 has a potential drawback relating to the durability of the seal. Over time, once the piston head 10 has been positioned in the barrel 30, the material of the barrier portion might exhibit creep in the region of the lip 13. That is, the material might begin to deform to take the shape of the barrel 30, decreasing the force pushing the lip 13 against the inner wall 34 of the barrel. As this process occurs, the quality of the seal around the piston head 10 will decrease.

The quality of the seal around the piston head 10 is particularly important in lab-on-a-chip applications such as nanopore applications. This is because such applications operate with very small volumes of fluid and so it is important that the amount of fluid being dispensed by a pump is dispensed as accurately as possible. The introduction of a weak seal in a pump reduces the accuracy of dispensing because fluid can leak around the plunger 21 instead of exiting the pump 1 through the orifice 31, without the operator's knowledge. As such, an experiment would proceed with the operator assuming a certain amount of fluid had been dispensed, when in fact a different amount had been dispensed.

Further, when charging the pump 1 by drawing fluid in through the orifice 31 a weak seal can cause a similar problem: instead of drawing in fluid, air from the pump surroundings can enter the barrel chamber 33 around the plunger 21 instead of fluid being drawn into the chamber 33 via the end of the barrel 31. Once again, the operator would not be aware of this, and so would assume a certain amount of fluid had been charged to the pump 1, when in fact a lesser amount had been charged.

The pump 1 at least partially overcomes these problems by the provision of a resilient member 15 behind the lip 13. That is, the resilient member 15 is provided on the opposite side of the barrier portion 11 to the barrier surface 12, and inside (i.e. closer to the centre of the piston head 10) the lip 13. The lip 13 thus projects at least partially around the resilient member 15. That is, as shown in the Figures, the lip 13 can extend around the resilient member 15, whilst part of the resilient member 15 can extend further away from the barrier portion 11 than the lip 13, in the axial direction of the piston, along the retaining portion 16. Increasing the distance that the resilient portion 15 extends along the retaining portion 16 increases the surface area provided between the two sections and thus increases the strength of any bond between the two sections.

The resilient member 15 can be an elastomeric material which resists compression and therefore the deformation of lip 13 as the plunger 21 is inserted into the barrel 30. As such, even if the barrier portion 11 and/or lip 13 is subject to material creep, the resilient member 15 will continue to resist its own compression and force the lip 13 back towards the inner wall 34 of the barrel 30. This maintains a good seal.

If the force resisting the deformation of the lip 13 is too strong, the pump 1 can become difficult to actuate. That is, if the lip 13 is pushed against the barrel 30 too strongly, it can become difficult to move the plunger 21 within the barrel, making the pump 1 stiff to operate. To prevent the pump 1 becoming too stiff, the lip 13 can be reduced in thickness. Reducing the thickness of the lip 13 reduces the hoop stresses in the lip 13 as it is deformed, and hence reduces the force with which the lip 13 resists deformation.

However, reducing the lip 13 thickness has an associated potential disadvantage that an overly thin lip 13 could be easily damaged, during either operation or assembly for example. If a lip 13 is too thin, any damage could lease to an incomplete seal being formed, and thus prevent the pump 1 working properly.

Therefore, rather than reducing the thickness of the entire lip 13 uniformly, it can be preferable to shape the lip to be tapered so as to thin towards the outer end of the lip 13. That is, the thickness of the lip 13 can varied to be thinner at the tip of the lip 13 and thicker where the lip joins the barrier portion 11. The tapering construction allows for a mechanically strong lip to be formed, which is resistant to damage and which also allows for a reduction in hoop stress in the region of the lip 13 towards the tip that will be deformed when the piston head 10 is inserted in the barrel 30.

The resilient member 15 can be elastic, such as a metal spring or an elastomeric material such as a silicone or a thermoplastic elastomer (TPE). One advantage of the construction of the piston head 10 is that, as long as the seal is functioning, the resilient member 15 does not come into contact with the fluid being pumped in and out of the chamber 33. As such, there is no direct contamination of the fluid by contacting the resilient member 15. However, as discussed above the use of metal may be undesirable in certain applications. Further, the use of elastomeric materials, such as TPE, may be preferred to assist in simplifying the manufacture of the piston head 10. For example, two-shot moulding could be used when employing an elastomeric resilient member.

Another advantage of the construction of the piston head 10 is that the resilient member does not come into contact with the inner surface 33 of the barrel 30. This is advantageous because it results in the contact between the plunger 21 and the barrel 30 occurring only around the lip 13 of the piston head 10. Since both the barrel 30 and the lip 13/barrier portion 11 are made of plastics materials the friction between the surfaces will be relatively low, compared to a convention syringe plunger seal in which the contact (and seal) occurs between the barrel and the elastic material of the sealing O-ring.

For example, Table 1 shows the dynamic coefficient of frictions for some plastics materials. In some cases, the coefficient of dynamic friction of PTFE relative to steel, measured according to ASTM D1894 can be 0.05 to 0.16. In some cases, the coefficient of dynamic friction of polypropylene relative to steel, measured according to ASTM D1894 can be 0.2 to 0.4. In some cases, the coefficient of dynamic friction of ETFE relative to steel, measured according to ASTM D1894 can be 0.3 to 0.74. In some cases, the coefficient of dynamic friction of PMMA relative to steel, measured according to ASTM D1894 can be 0.15 to 0.8. Preferable materials for the barrier portion and the barrel have a coefficient of dynamic friction relative to steel of 0.4 or less, preferably 0.2 or less, measured in accordance with ASTM D1894.

TABLE 1

Coefficients of dynamic friction of some materials

| Material | Coefficient of Dynamic Friction |
| --- | --- |
| UHMWPE | 0.1-0.2 |
| PTFE | 0.05-.1 |
| FEP | 0.08-.3 |
| Polypropylene | 0.3-0.4 |
| HDPE | 0.07-0.4 |
| Ethylene tetrafluoroethylene (ETFE) | 0.3-0.4 |
| PMMA | 0.5-0.8 |
| Polycarbonate | 0.3-0.9 |
| Nylon | 0.2-0.5 |
| Acetal | 0.1-0.4 |
| Acrylonitrile butadiene styrene (ABS) | 0.2-0.5 |
| NexPrene (RTM) thermoplastic vulcanizates | 0.4-0.5 |

However, as can be seen from the table, plastics can have higher coefficients of friction. In particular, softer materials more commonly used as seal materials are likely to have higher coefficient of materials. For example, the coefficient of friction of silicone rubber is anecdotally close to 1, and special materials (such as NexPrene® listed in Table 1) have been developed to try and obtain similar elastomeric properties to silicone whilst exhibiting lower coefficients of friction that silicone. However, as shown in Table 1, the coefficient of friction of materials such as NexPrene is not as low as materials such as PTFE or UHMWPE for example.

As a result, the piston seal of the invention can reduce occurrence of stick-slip when the pump is driven by using materials to form the seal that are not conventionally suitable. This is due to the different construction of the seal, compared to conventional seals that provide a resilient or energised seal without bringing the material providing resilience into contact with the barrel. This results in both a smoother pumping operation and also a lower driving force being required to actuate the pump. This in turn results in lower pressures in the pump chamber 33 and so smaller amounts of air compression and more accurate dispensing.

Another way of lowering the friction between the piston and the barrel is to provide a suitable surface treatment on either the barrel or the piston, or both. The surface treatment can introduce a texture that reduces the overall area of contact between the piston and the barrel, and thus the friction acting between those surfaces. On the other hand, the surface is preferably not textured so much as to compromise the quality of the seal. As such, the ideal surface finish may be material dependent. However, for example, a sparked surface finish of 30 VDI (according to the Verein Deutscher Ingenieure 3400 Guideline, equivalent to an arithmetic mean roughness value, $R_a$, of 3.2 µm) of on the plunger seal surface/lip 13 and a polished barrel surface can be effective, particularly on a polycarbonate barrel for example. More generally a sparked surface finish of 18 VDI ($R_a$ 0.8 µm) to 39 VDI ($R_a$ 9 µm) may be effective on the plunger seal surface/lip 13.

As such, the piston head 10 provides a strong lasting seal by the provision of the resilient member 15 behind the lip 13, whilst also avoiding the pump becoming too stiff to actuate smoothly and accurately.

The resilient member 15 is positioned between the lip 13 and the retaining portion 16 of the piston head 10. As such, the resilient member is compressed against the retaining portion 16 when the lip 13 is pushed back, and this can hold the resilient member 15 in place. However, it can be preferable to further secure the resilient member 15 in place, to avoid it working loose during use. For example, the resilient member may be attached to the barrier portion 11 or the restraining member 16 by chemical means such as an adhesive. Alternatively, or in combination with an adhesive, the piston head can be shaped to mechanically hold the resilient member 15 in place. As can be seen in FIG. 2, the inside surface of the lip 13 is shaped to have an overhang 16 which projects radially inwards and above the surface immediately below it. This allows for a resilient member 15 to be positioned under the overhang 16, and thus secured in place by the overhang 16 acting as a physical blockage to the resilient member 15 moving out of place. This effect is increased as the lip 13 is deformed inwardly, moving the overhang further inwards.

The barrier portion 11 and the retaining portion 16 can be made of a plastics material and preferably for nanopore applications uses a plastics material that exhibits low chemical/plasticiser leaching. Possible plastics include polytetrafluoroethylene (PTFE), ultra-high-molecular-weight polyethylene (UHMWPE), polypropylene (PP), perfluoroalkoxy (PFA) or fluorinated ethylene propylene (FEP).

UHMWPE is a preferable material for forming the barrier portion 11 and resilient member 16 because is exhibits a relatively low amount of creep, whilst also being mouldable.

Moulding is a preferred manner of producing the piston head 10, because it is allows mass manufacture of substantially identical products. Further, moulding enables the formation of the resilient member 15 within the lip 13 in a way that ensures that the resilient member fills the available space and is securely positioned (e.g. under any overhangs). A moulding process may include first moulding the barrier portion 11/retaining portion 16 as an integrated structure that includes all the features of the lip 13, using a plastics material such as UHMWPE. Thereafter, in a second moulding step, the resilient member 15 may be formed by moulding the resilient member 15 into the region between the lip 13 and the retaining portion 16. As such the material used to form the resilient member (TPE for example) will flow under any overhangs 16, for example, before setting in position.

Such a two stage process not only produces a good fit between the resilient member 15 and the rest of the piston head 10, but also produces a good bond between the two sections. The moulding can be carried out as part of two-stage over-moulding process, using different tools for each moulding step. Alternatively, the bond between the two sections can be further improved by using a two-shot moulding process that utilises the same tool for both moulding operations. A two-shot moulding process preferably allows for the formation of the resilient member 15 without exposing the material of the resilient member 15 on the barrier surface 12. For example, the material for the resilient member 15 can be injected into position through the retaining portion 16 or through the barrier portion 11 from the piston side (using channels to allow the material to pass through the barrier portion 11 to behind the lip 13 at the periphery of the barrier portion 11).

The piston 20 is driven by an actuating assembly 40, and specifically by the actuating member 41. In one arrangement, the piston 20 is provided with an engagement section, comprising a slot 25, for engaging with the actuating member 41. As shown in the Figures, this section can be provided with ribs 23 to support the slot 25 and to ensure that the slot remains rigid, but the slot could alternatively be provided in a solid section of the piston 20.

The slot 25 has two substantially parallel and flat sides. The actuating member 41 also has two substantially parallel and flat sides, having a double-D cross-sectional shape (i.e. two flat sides opposite each other and two outwardly convex curved sides opposite each other) as visible in FIG. 4b. When the flat sides of the actuating member 41 are parallel with the flat sides of slot 25, the actuating member 41 can slide into the slot 25. Once in position in the slot 25, turning the actuator rod 41 will then turn the piston 20 assembly via the flats.

In practice, a fluidics circuit may involve several fluids and require several pumps. By using pump assemblies 1, the circuit can be arranged with the slots of all the pumps facing in the same direction, to allow easy connection to (and subsequent disconnection from) actuating members by relative motion of the pumps towards the actuating members 41 in a direction substantially perpendicular to the direction in which the piston 20 travels along the barrel 30. That is, the pumps can be engaged by the actuating members 41 in a sideways fashion. This avoids the need, for example, for the provision of any mechanism to initiate engagement in the direction of piston travel. This further reduces the height (in the arrangement of the Figures) that the system occupies. Such an arrangement provides space saving advantages whilst being relatively easy to construct, by providing the hollow plunger. Alternatively, the actuator 41 could be hollow, or have branched sections from the main actuator drive shaft, so as to engage with the outer surface of the piston 20 (e.g. by providing an actuating member 41 that slots over and/or around the piston). In this arrangement, the outer surface of the piston can be provided with structural features, such as flat surfaces, to allow engagement with the actuator 41 so that the actuator 41 can turn the piston 20. As this piston is turned, it can rise up through/within the actuator 41. Such an arrangement can maintain the space-saving advantages of the arrangement shown in the Figures. This arrangement may be preferable, for example, if the pump volume is small enough that the arrangement shown in the Figures would result in an actuator 41 that was insufficiently strong. That is, if the space within the plunger became so small that an actuator 41 of a particular desired material became too thin and began to flex and/or twist itself rather than drive piston 20. In that case, the actuator could be provided outside the piston 20, allowing the actuator to be thickened and strengthened whilst maintaining the small pump volume.

Another space saving feature is the provision of a hollow space within the plunger 21. This allows for the piston 20 to rise around the actuating member 41 as the piston 20 is withdrawn. That is, there is no need to withdraw the actuating member 41 at the same time as withdrawing the piston 20, because the actuating member can extend into the hollow plunger 21. As a result, there is no need to provide any mechanism to enable the withdrawing of the actuating member. The alternative, of moving the actuating member 41 with the piston 20 would require extra mechanisms (to enable the motion) that would take up extra space. Therefore, once again, the described arrangement assists in reducing the height of the system.

The longitudinally stationary nature of the actuating member 41 also allows for the motor 60 to be coupled to the actuating member 41 via a worm gear 50. Further the motor 60 can be provided to produce a rotational driving with an axis of rotation substantially perpendicular to the eventual direction of travel of the piston 20 with respect to the barrel 30, as discussed in more detail below. As a result, the motor can be positioned (e.g. in the arrangement of FIG. 1) to the side of the actuating mechanism 40 rather than in a conventional position which would linearly interpose an actuating mechanism between a motor and a piston.

To operate the pump system various motors and control systems could be used. In the case of pumping for fluidic and nanopore applications a stepper motor system can be preferable. This is because stepper motors give a high torque output at low speeds with high positional repeatability. Use of a stepper motor therefore allows good control when pumping at slow rates. Stepper motors are also inexpensive compared with other motion control systems, due to there being no required feedback to the motion controller. Low cost is important when multiple motors per system are required, as in the case where there are multiple fluids to control in a nanopore application.

When using a stepper motor in the pump system, the lowest output rate that can be provided by the pump is also determined by the motor controller. Controllers are usually limited by how many steps they can move per time interval, for example 1 step/s. Therefore to help achieve very low pumping speeds it is more preferable to use a stepper motor that has a high number of steps per revolution and a controller that has micro stepping capability. Micro stepping capability allows the controller to move a set number of smaller steps for each motor step.

Size constraints for the motor 60 can also be a consideration in fluidic and nanopore applications. This makes it preferable to use a stepper motor selected with a high power to size ratio.

An example of a motor that could be used as motor 60 is the Faulhaber Stepper Motor AM2224-AV-4.8, which has an outside diameter of 22 mm, a holding torque of 26 mNm and 24 steps per revolution (or 15° per step). Of course, alternative motors of similar specifications can also be used. Such a motor can be used in combination with a controller such as the Allegro A3987 DMOS Micro Stepping Driver, which has the capability to move the motor 16 micro-steps per step. In combination, this gives a total of 384 micro-steps per revolution (or 0.94° per micro-step) and allows a low speed of 1 micro-step per second. The small stepping speed and low change of angle per micro-step translates into fine control of the pump output speed.

The provision of the worm gear 50, which drives the gear of the actuating mechanism 40, also allows for a suitable gearing ratio to be selected for the desired operation. As a result, for example, it is possible to provide very fine control of the pump position by providing a gearing ratio that translates many turns of the worm gear 50 into few turns of the gear of the actuating assembly 40. For example, a range of gearing ratios from 1:1 to 50:1 could be appropriate for fluidics and nanopore applications. In addition, the pitch of the screw thread between the piston sheath 22 and the barrel 40 can also be varied to affect how much rotation of the piston is required to produce a certain amount of longitudinal motion. In a particular preferred arrangements, the Faulhaber Stepper Motor AM2224-AV-4.8 is used with the Allegro A3987 DMOS Micro Stepping Driver, in combination with a gearing ratio of 35:1, a screw thread pitched to produce 1 mm longitudinal movement per revolution and a barrel width of 11 mm. This allows for the pump to be controlled to provide flow rates across a range of from 0.1 µl/s to 100 µl/s.

An example of the operation of the pump assembly 1 is discussed below. The skilled reader will understand that this particular method of operation is not limiting upon the invention.

The pump barrel 30 can be integrated with a fluidics circuit, with a fluid inlet/outlet 31 from the barrel 30 connecting to a flow path in the fluidics circuit, as shown in the Figures. However, in alternative designs, separate inlets and outlets could be provided (with non-return valves to prevent flow in the wrong direction). When decoupled from the actuating mechanism 40, the piston 20 can be provided screwed onto the barrel until the lugs 24, 34 come into contact with each other. In this state, the piston plunger 21 and head 10 are advanced as far as possible in the barrel 30, thereby minimising the volume of fluid in the barrel 30 (preferably so that the barrel 30 is empty of fluid).

The pump barrel/piston combination can be engaged with a driving member 41. The driving member 41 may be part of a larger mechanism or machine. The machine may be configured to provide the driving member in a particular (rotational) orientation, so that the flat sides of the driving member 41 are arranged at a particular position to allow the slot 25 of piston 21 to slide around the base of the driving member 41. The piston 21 can slide around the driving member 41 until the driving member 41 is positioned in the slot 25, so that an axis of rotation of the driving member is substantially coincident with an axis of rotation of the piston 20.

Once the pump barrel/piston combination is engaged with the driving member 41, the pump assembly 1 is ready for operation. The motor 60, arranged with its rotational axis substantially perpendicular to the direction of longitudinal travel of the piston 20 along the barrel 30, can be operated to produce a rotational driving force for the worm gear 50. The worm gear 50 is coupled to the actuating assembly 40 via a gear. The gear is positioned at the opposite end of the actuating member 41 to the end of the actuating member 41 that fits into slot 25 of the piston 20.

The rotation of the worm gear 40 causes the actuating assembly gear to rotate, and therefore produces a rotational motion of the actuating member 41, having an axis of rotation that is substantially perpendicular to the axis of rotation of the worm gear 50.

As mentioned above, the slot 25 of the piston is positioned around the actuating member 41, so the rotation of the actuating member causes a rotational force to be applied piston 20.

If the rotational force is applied to the piston in a direction that urges the lugs 24, 34 together, the piston 20 will not move because it is already rotationally advanced as far as it can in that direction. Optionally, the assembly 1 can be provided with a feedback system to detect the non-rotation of the piston 20 and stop (or reverse) the motor 60. Alternatively, a mechanism may be employed to keep track of the rotational position of the piston to avoid the piston 20 being urged past its most advanced point.

If the rotational force is applied to the piston in a direction that urges the lugs 24, 34 apart (i.e. in the direction which will withdraw the plunger 21 and head 10 within the barrel 30), the piston 20 is free to rotate along the complementary threads of the sheath 22 and barrel 30. As such, the rotational force applied to the piston 20 via the slot 25 and the actuating member 41 causes rotation of piston 20 that is translated into longitudinal motion (i.e. motion along the axis of rotation) by the threaded surfaces.

The longitudinal motion results in the plunger 21 and head 10 being withdrawn within the barrel 30. As previously mentioned, the head 10 can be connected to the plunger 21 in a manner that allows rotation of the head 10 relative the piston 20. If so, the head 10 may move within the barrel so as to maintain its rotational orientation with respect to the barrel 30 (due to the friction between the barrel 30 and the head 10), and rotate with respect to the piston 20/plunger 21.

If the opening 31 in the barrel 30 is connected to a fluid supply, the fluid will be drawn into the barrel as the plunger 21 and head 10 are withdrawn. This is because the head 10 provides a seal across the barrel 30 that prevents any fluid (e.g. air) entering the space vacated in the barrel from the plunger side of the head 10, and so the suction pressure generated by withdrawing the head draws fluid in through the opening 31.

The longitudinal motion also results in a change in the relative position of the piston 20 to the actuating member 41. That is, as the piston 20 and the actuating member 41 rotate together, the longitudinal motion of the piston 20 causes the piston to move along the actuating member 41 (i.e. move upwardly in the arrangement of FIG. 1). This is enabled by the provision of a hollow space within the plunger 21, into which the actuating member 41 can extend through the slot 25. Therefore, as the piston 20 rotates it travels along the actuating member 41, accepting the actuating member 41 further into the hollow plunger 21.

Figure 9:
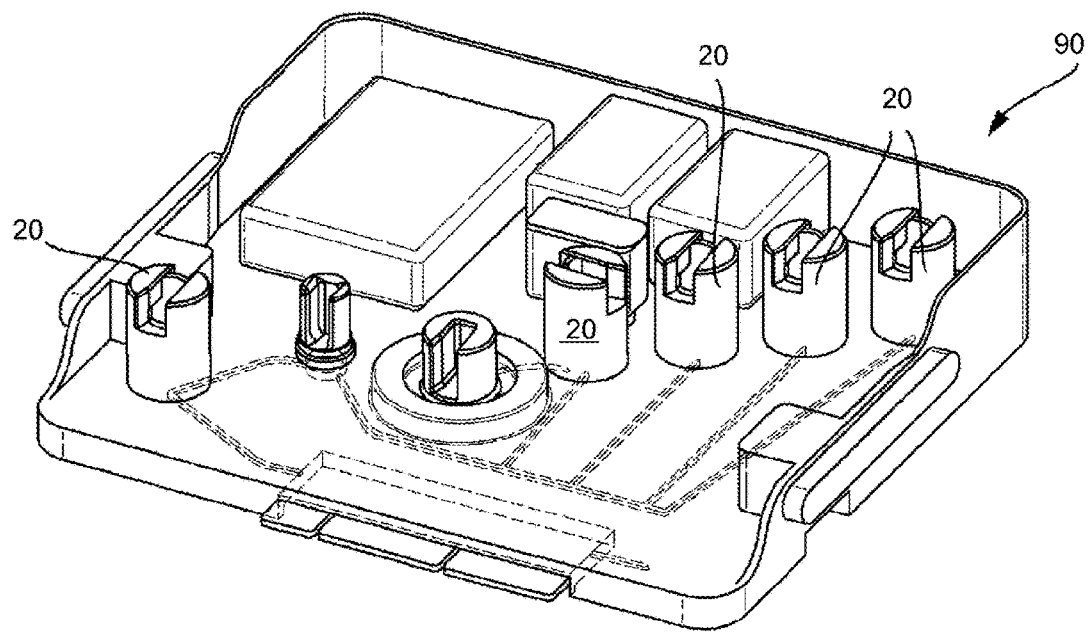
FIG. 9 is a perspective view of a cartridge for use with an analysis unit.

As the piston 20 moves along the actuating member 41, the actuating member 41 will begin to extend beyond the slot 25, and so it does not remain possible to disengage the piston 20 from the actuating member 41 by lateral motion (i.e. motion perpendicular to the rotation axis of the piston 20). Therefore, the pump piston/barrel can become locked into the machine housing the actuating mechanism 40 until the piston 20 is returned to its original position. When the piston is advanced within the barrel as shown in FIG. 3a, the driving member may be disengaged from slot 25. This allows for the removal of the barrel and piston that have been contaminated with fluid sample and the subsequent replacement of a new barrel and piston without having to move the driving member longitudinally. This also enables the other components of the pump such as the drive and motor to be reused. A cartridge 90, for use with an analysis apparatus, comprising a plurality of pumps, amongst other features, may be provided as illustrated in FIG. 9 (in which the pistons 20 are visible, covering the various barrel portions 30). The entire cartridge may thus be removed and replaced from a surrounding housing or body that contains the driving members 41 and the associated drive mechanisms.

Once sufficient fluid has been drawn into the barrel 30, the motor 60 can be halted. The fluid will be held in the barrel 30 until motion of the motor 60 is re-started. The motor 60 can be re-started in the opposite direction to its previous motion, in order advance the plunger 21 and head 10 within the barrel 30 and force the fluid out of the opening 31. This may be desirable, for example, if the fluids circuit 31 can be reconfigured after fluid has been stored in the barrel 30, to provide a different flow path to the opening 31, along which it is desirable to provide the fluid.

Because the pump assembly 1 translates the rotational driving force into a longitudinal motion of the piston, fine control of the amount of how fluid is expelled (or, indeed, drawn in) through opening 31 is possible. Therefore, the motor 60 can be restarted to provide, for example, a known number of turns of the worm screw 50, which will translate into a certain (known) longitudinal displacement of the piston 20. If the dimensions of the barrel 30 are known, the volume of fluid displaced (and forced into the fluidics circuit) will also be known. Therefore, the pump assembly 1 can be used to provide metered amounts of fluids. In an alternative operation, by controlling the speed at which the motor 60 turns the worm gear 50, and thus the piston 20, the pump assembly 1 can be used to provide a specific flow rate of fluid through the opening 31. In practice, it can be desirable to control both the flow rate of fluid and the total amount of fluid delivered simultaneously, and the pump assembly 1 makes this possible.

The fluid in the barrel 30 may be expelled all at once, or in increments. The fluid may also be replenished before it is all expelled (by using the motor to withdraw the piston 20 further). It is also possible for the fluid in the barrel 30 to be changed if the fluidics connected to the opening 31 can be changed. For example, a first fluid may be drawn into the barrel 30 and subsequently expelled, the fluidics circuit connected to the opening 31 could be reconfigured and a new fluid supply connected to be drawn in.

Once the piston 20 has been advanced back to the point at which the lugs 24, 34 meet, it is possible to disengage the pump barrel/piston combination from the actuating assembly 40.

As will be understood from the foregoing description, the pump assembly 1 allows for the accurate provision of amounts of fluid, whilst also maintaining a low pump profile, by employing a design that reduces the required longitudinal space for providing actuation and by translating the rotational motion of the piston 20 into a longitudinal motion by use of the screw thread. The construction also allows for the pump parts to be produced cheaply, without compromising the accuracy of fluid delivery, which in turn provides the possibility of the pump being used disposably.

In practice, the pump and drive train shown in the Figures will be contained within a casing, as part of a system such as a fluidics or nanopore system. The construction of the pump and actuator 41 allows for the actuator 41 to be mounted in the casing so that it is rotatable, but otherwise held stationary, with respect to the casing. That is, the actuator 41 is held translationally stationary. As a result, there is no need to provide any extra space in the casing to allow for translational motion of the actuator 41 during pumping. Instead, as the piston is driven by the rotational motion of the actuator 41, the actuator 41 remains in the same translational position with respect to the casing. The barrel 30 can also be held stationary within the casing, allowing easy connection to any fluidic system as required.

The system can be arranged so that the pump can be introduced within the casing, on a cartridge for example. In such a system, the loading of the cartridge may bring the pump on the cartridge into engagement with the actuating member.

In such systems, it may be preferable to save space in the system by reducing the width or height of the opening in the casing, through which the cartridge is inserted, as far as possible. In that case, it may be preferable for the pump on the cartridge to be introduced in an 'empty' configuration with the plunger advanced as far into the barrel as possible. In that case the pump will present the lowest profile on the cartridge. As cartridge profile will depend upon cartridge components, including the pump, reducing the profile of the pump contributes to providing a lower overall cartridge profile. A reduction in cartridge profile allows a corresponding reduction in the size of the opening through which the cartridge is inserted into the casing, and so can contribute to a reduction in the overall system size. Once the cartridge has been inserted, and the pump is brought into engagement with the actuating member, the pump can be raised around the actuating member and operated as discussed above.

In other cases, it may be preferable to insert the cartridge with the pump pre-filled. In those cases, the pump will present a larger profile because the piston will be withdrawn out of the pump and so project further 'up' (in the sense of the accompanying Figures). In that case a larger slot for the cartridge would be required.

Although the system has been described above with respect to a single pump on a cartridge, some systems may utilise a plurality of pumps that are all provided on a single cartridge.

The present invention has been described above with reference to specific embodiments. It will be understood that the above description does not limit the present invention, which is defined in the appended claims.

The invention claimed is:

1. A pump comprising:
   a barrel for holding fluid;
   a piston for drawing fluid into the barrel and driving fluid out of the barrel, wherein the piston comprises a plunger configured to move within the barrel and a sheath configured to move around an outer surface of the barrel; and
   a driving member;
   wherein an inner surface of the sheath and the outer surface of the barrel have complementary screw threads so that, in use, rotating the piston causes the piston to travel along the barrel; wherein the piston comprises an engagement section for engaging with the driving member and enabling the driving member to turn the piston, and wherein the engagement section comprises a slot for engaging the driving member by relative motion between the piston and the driving member in a direction substantially perpendicular to the direction of travel of the piston along the barrel.

2. The pump according to claim 1, wherein the plunger is hollow.

3. The pump according to claim 2, wherein the engagement section comprises an opening into the hollow plunger.

4. The pump according to claim 1 wherein, in use, the driving member is held translationally stationary with respect to the piston and barrel whilst the piston is moved relative to the barrel.

5. The pump according to claim 1, wherein the driving member has two flat and substantially parallel sides for engaging the engagement section.

6. The pump according to claim 2, wherein the pump is configured such that, in use, the driving member extends within the hollow plunger as the piston travels along the barrel.

7. The pump according to claim 1, wherein the driving member, in use, moves rotationally with respect to the barrel to drive the piston within the barrel.

8. The pump according to claim 1 further comprising a gear arranged to rotate the driving member, the gear being arranged to rotate with an axis of rotation substantially perpendicular to the axis of rotation of the driving member.

9. The pump according to claim 8 wherein the gear is a worm gear.

10. The pump according to claim 1, further comprising a stepper motor arranged to drive the driving member.

11. The pump according to claim 1, further comprising a piston head for forming a seal against an inner surface of the barrel, wherein the piston head is connected to the plunger of the piston so that the piston head is free to rotate with respect to the plunger or the barrel.

12. The pump according to claim 1, wherein the pump is configured to resist rotation of the piston relative the barrel at a predetermined position.

13. The pump according to claim 1, wherein the sheath is provided with a lug for resisting rotation of the piston relative to the barrel when the lug is brought into contact with another portion of the pump.

14. The pump according to claim 1, further comprising a driving member that engages the outer surface of the piston.

15. The pump according to claim 1, wherein the barrel comprises or consists of acrylonitrile butadiene styrene, polycarbonate, polytetrafluoroethylene, ultra-high-molecular-weight polyethylene, polypropylene, perfluoroalkoxy, poly(methyl methacrylate) or fluorinated ethylene propylene.

16. The pump according to claim 1 wherein the piston comprises acetal and/or polybutylene terephthalate.

17. The pump according to claim 16, wherein the piston further comprises glass fibre and/or polytetrafluoroethylene.

18. An analysis apparatus comprising a body and a cartridge attachable to the body, wherein the cartridge comprises a pump and wherein the body comprises a driving member for engaging with the pump;
wherein the pump comprises a barrel for holding fluid, and a piston for drawing fluid into the barrel and driving fluid out of the barrel;
wherein the piston comprises a plunger configured to move within the barrel and a sheath configured to move around an outer surface of the barrel;
wherein an inner surface of the sheath and the outer surface of the barrel have complementary screw threads so that, in use, rotating the piston causes the piston to travel along the barrel; and
wherein the piston comprises an engagement section for engaging with the driving member and enabling the driving member to turn the piston, wherein the engagement section comprises a slot for engaging the driving member by relative motion between the piston and the driving member in a direction substantially perpendicular to the direction of travel of the piston along the barrel.

19. An analysis apparatus according to claim 18 wherein the cartridge comprises a plurality of pumps and the body comprises a plurality of respective driving members.

20. An analysis apparatus according to claim 18 wherein the body further comprises a gear for rotating the driving member and a stepper motor for driving the driving member.

* * * * *